US010173898B2

(12) United States Patent
Blanford et al.

(10) Patent No.: US 10,173,898 B2
(45) Date of Patent: Jan. 8, 2019

(54) FUNCTIONALIZED GRAPHENE

(71) Applicant: THE UNIVERSITY OF MANCHESTER, Manchester (GB)

(72) Inventors: Christopher Blanford, Manchester (GB); Mirja Wehner, Munich (DE); Sabine Flitsch, Manchester (GB)

(73) Assignees: Christopher Blanford, Manchester (GB); Sabine Flintsch, Manchester (GB); Mirja Wehner, Munich (DE)

(*) Notice: Subject to any disclaimer, the term of this patent is extended or adjusted under 35 U.S.C. 154(b) by 0 days.

(21) Appl. No.: 15/308,446

(22) PCT Filed: May 11, 2015

(86) PCT No.: PCT/GB2015/051376
§ 371 (c)(1),
(2) Date: Nov. 2, 2016

(87) PCT Pub. No.: WO2015/170124
PCT Pub. Date: Nov. 12, 2015

(65) Prior Publication Data
US 2017/0081195 A1 Mar. 23, 2017

(30) Foreign Application Priority Data
May 9, 2014 (GB) .................................. 1408221.8

(51) Int. Cl.
C01B 31/00 (2006.01)
C07H 15/04 (2006.01)
(Continued)

(52) U.S. Cl.
CPC ........ C01B 31/0484 (2013.01); C01B 32/186 (2017.08); C01B 32/19 (2017.08);
(Continued)

(58) Field of Classification Search
CPC ... C07H 15/04; C01B 31/0484; C01B 32/186; C01B 2/19; B82Y 30/00; B82Y 40/00;
(Continued)

(56) References Cited

U.S. PATENT DOCUMENTS

| 2013/0018204 A1 | 1/2013 | Jeon et al. |
| 2013/0045897 A1 | 2/2013 | Chakraborty et al. |
| 2013/0108540 A1* | 5/2013 | Baek .................... C01B 31/0469 423/448 |

FOREIGN PATENT DOCUMENTS

WO 2013040356 A1 3/2013

OTHER PUBLICATIONS

Eda, et al., Large-area ultrathin films of reduced graphene oxide as a transparent and flexible electronic material, Nature Nanotechnology 2008; 3: 270-274.*

(Continued)

Primary Examiner — Daniel McCracken
(74) Attorney, Agent, or Firm — O'Connor & Company; Ryan P. O'Connor

(57) ABSTRACT

Graphene is chemically modified by a process resulting in the introduction of functional groups located only at an edge of the graphene plane. The functionalized graphene finds uses in numerous applications and further chemical synthesis, including a process for coupling an organic or inorganic moiety to the graphene plane via the edge-located functional group. The disclosed products and processes provide highly flexible platforms for the integration of graphene into a variety of applications.

11 Claims, 12 Drawing Sheets

(51) Int. Cl.
    *C01B 31/04*         (2006.01)
    *C01B 32/186*       (2017.01)
    *C01B 32/19*         (2017.01)
    *C01B 32/194*       (2017.01)
    *B82Y 30/00*         (2011.01)
    *B82Y 40/00*         (2011.01)
    *B82Y 5/00*          (2011.01)

(52) U.S. Cl.
    CPC ........... *C01B 32/194* (2017.08); *C07H 15/04* (2013.01); *B82Y 5/00* (2013.01); *B82Y 30/00* (2013.01); *B82Y 40/00* (2013.01); *Y10S 977/734* (2013.01); *Y10S 977/847* (2013.01); *Y10S 977/915* (2013.01)

(58) Field of Classification Search
    CPC .... B82Y 5/00; Y10S 977/734; Y10S 977/847; Y10S 977/915
    See application file for complete search history.

(56) References Cited

OTHER PUBLICATIONS

Gilje, et al, A Chemical Rout to Graphene for Device Applciations, Nano Letters 2007; 7(11): 3394-3398.*

Jeon et al., "Large-Scale Production of Edge-Selectively Functionalized Graphene Nanoplatelets via Ball Milling and Their Use as Metal-Free Electrocatalysts or Oxygen Reduction Reaction", J.Am. Chem.Soc. 2013, 135, 1386-1393.

* cited by examiner

FUNCTIONALIZED GRAPHENE

INTRODUCTION

The present invention relates to functionalised graphene and graphene conjugates, as well as to processes for their preparation, and to their uses.

BACKGROUND OF THE INVENTION

Graphene, an aromatic graphite monolayer first isolated in 2004[1] has become famous as a highly versatile material with unique properties in terms of mechanical strength, electrical conductivity and thermal conductivity[1]. Its flexibility makes it perfectly suited for coatings and application in membranes[2]. All these desired properties are at least partly dependent on the two dimensional structure of the carbon allotrope.

Many approaches to the chemical modification of graphene have been made to fine-tune its electrical properties[3], its water solubility[4] and to introduce functional groups. The Hummers method[5] followed by reduction[6] is a well-known way to produce reduced graphene oxide, a graphene derivative, which contains functional groups for further modification. Chua and co-workers have performed Friedel-Crafts alkylation and acylation reactions on reduced graphene oxide[7]. In these reactions, new C—C bonds are formed and the introduction of functional groups is mediated through this linker chain. Other methods include covalent coupling of functional groups to the basal plane of the graphene sheet using e.g. Diels-Alder reactions[8] or diazonium chemistry[9], or non-covalent adhesion via π-π stacking[10, 11]. However, many of these treatments compromise a characteristic feature of graphene: its two-dimensional structure, and most involve disruption of the graphene π-system, thus changing its electrical properties.

Other attempts to achieve successful edge functionalization of graphene have focused on planetary ball milling techniques[12, 13, 14, 15]. However, the high-energy, indiscriminate nature of these techniques, in which functionalization is performed in-situ during milling of the graphite starting material, has a number of drawbacks, most notably a lack of chemical control over the functional groups that are ultimately introduced.

In view of the above-discussed deficiencies, there remains a need for a controlled, more direct means of chemically modifying graphene, whilst simultaneously preserving its interesting and desirable properties for exploitation in further synthesis and applications.

The present invention was devised with the foregoing in mind.

SUMMARY OF THE INVENTION

According to a first aspect of the present invention there is provided functionalised graphene comprising at least one functional group covalently bonded directly to an edge of a graphene plane, wherein the functional group is only selected from the group consisting of —$NO_2$, —$NH_2$, —$SO_3H$, halide, —$N_3$, —MgBr and —SH, and wherein the functional group is only bound to an edge of the graphene plane.

According to a second aspect of the present invention there is provided a process for the preparation of functionalised graphene as defined herein, the process comprising the steps of:

a) preparing a sample of graphene to be functionalised,
b) contacting the graphene with one or more reagents suitable for introducing at least one functional group selected from the group consisting of —$NO_2$, —$NH_2$, —$SO_3H$, halide, —$N_3$, —MgBr and —SH to any available edge of the sample of graphene, and
c) isolating the functionalised graphene bearing only the at least one functional group selected from the group consisting of —$NO_2$, —$NH_2$, —$SO_3H$, halide, —$N_3$, —MgBr and —SH.

According to a third aspect of the present invention there is provided a graphene conjugate comprising at least one organic or inorganic moiety covalently attached to the at least one functional group of the functionalised graphene as defined herein.

According to a fourth aspect of the present invention there is provided a graphene conjugate, wherein the graphene conjugate is formed by reaction of at least one organic or inorganic moiety with the at least one functional group of the functionalised graphene as defined herein.

According to a fifth aspect of the present invention there is provided a process for the preparation of a graphene conjugate as defined herein, the process comprising the steps of:

a) preparing a sample of functionalised graphene in accordance with a process defined herein,
b) reacting the functionalised graphene with at least one organic or inorganic moiety such that the organic or inorganic moiety is covalently attached to the graphene via one or more of the functional groups present on the functionalised graphene, and
c) isolating the graphene conjugate.

According to a sixth aspect of the present invention there is provided a use of functionalised graphene defined herein or a functionalised graphene conjugate defined herein for identifying defects present in the graphene plane.

According to a seventh aspect of the present invention, there is provided functionalised graphene obtainable, obtained or directly obtained by a process described herein.

BRIEF DESCRIPTION OF THE DRAWINGS

Embodiments of the invention will now be described, by way of example only, with reference to the accompanying figures, in which.

DETAILED DESCRIPTION OF THE INVENTION

Graphene

Figure 1:
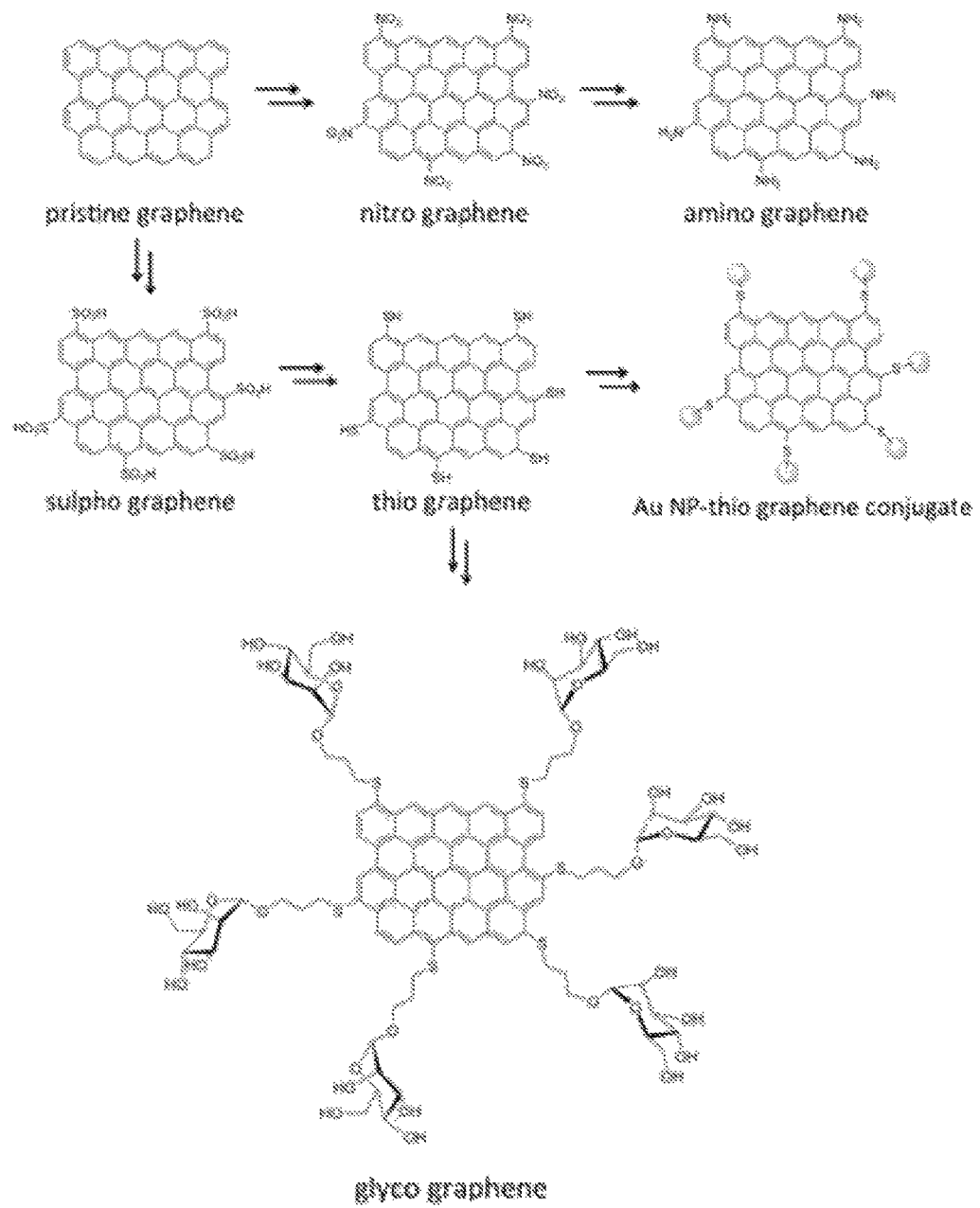
FIG. 1 shows the structure of functionalised graphene and graphene conjugates of the present invention.

Graphene is the name given to a particular crystalline allotrope of carbon in which each carbon atom is bound to three adjacent carbon atoms (in a $sp^2$ hybridised manner) so as to define a one atom thick planar sheet of carbon. The carbon atoms in graphene are arranged in the planar sheet in a honeycomb-like network of tessellated hexagons. Graphene is often referred to as a two-dimensional structure because it represents a single sheet or layer of carbon of nominal (one atom) thickness. Graphene can be considered to be a single sheet of graphite.

In the present invention, the term "graphene" will be understood to refer to single layers of pristine graphene or thin stacks of two to ten pristine graphene layers, including few-layer-graphene (FLG, approximately 3 nm thick). Such materials may collectively be referred to as "graphene-family nanomaterials". The thin stacks of graphene are distinguished from graphite by their thinness and a difference in physical properties. In this regard, it is generally acknowledged that crystals of graphene which have more than 10 molecular layers (i.e. 10 atomic layers; 3.5 nm) generally exhibit properties more similar to graphite than to graphene. Thus, throughout this specification, the term graphene is intended to mean a carbon nanostructure with up to ten graphene layers.

In certain embodiments, the definition of "graphene" may also encompass ultrathin graphite (graphite having a thickness of less than 100 nm).

For the avoidance of doubt, the term graphene used herein does not encompass graphene oxide.

Functionalised Graphene

As described hereinbefore, in a first aspect the present invention provides functionalised graphene comprising at least one functional group covalently bonded directly to an edge of a graphene plane, wherein the functional group is only selected from the group consisting of —$NO_2$, —$NH_2$, —$SO_3H$, halide, —$N_3$, —MgBr and —SH, and wherein the functional group is only bound to an edge of the graphene plane.

The functionalised graphene of the present invention presents a variety of advantages over similar materials taught by the prior art. Chiefly, the functionalised graphene of the present invention contains functional groups bound only to edges of the graphene plane, without therefore compromising the surface structure of the graphene plane. Unlike for functionalization of reduced graphene oxide, the topological specificity giving rise to the functionalised graphene of the present invention allows graphene's desirable characteristics stemming from its two-dimensional structure, including its electronic properties, to be preserved. In contrast, high-energy, indiscriminate ball-milling techniques inherently result in functional groups being introduced to the basal plane of graphene, thereby compromising its interesting properties. Without wishing to be bound by theory, and noting that such ball-milling techniques can only introduce functional groups at sites where C—C bonds have been fractured by the mechanical force of milling, it is believed that such basal plane functionalization (as opposed to edge functionalization) arises due to the comparatively lower amounts of energy required to create a single point defect within the graphene plane (thereby leaving such a basal plane site open to functionalization) when compared with the amount of energy required to create a new graphene flake having a newly-formed edge. Moreover, the high-energy nature of such techniques translates to a lack of control over the exact nature of the functional group being introduced to graphene. In addition, mechanically fractured C—C bonds that are not functionalised in the manner intended are then susceptible to reaction with atmospheric moisture and/or oxygen, which results in graphene that has been modified with a variety of unwanted functional groups.

In addition to the above, the functionalised graphene of the present invention represents an improvement on prior art materials since the functional groups are bound directly to the edge of the graphene plane, without the need for an intermediary linker moiety, which might compromise or impede the material's reactivity in further synthesis or its performance in an end application. Moreover, direct linking of the functional group to the graphene plane improves electron transport between the graphene sheet and moieties bonded thereto through the functionality. Aside from the above-discussed advantages, depending on the nature of the functional group bound to the graphene, the solubility and dispersibility of graphene in solution, or the wettability properties of graphene-coated surfaces, can be tailored according to a particular application or further synthetic process. For example, sulpho-graphene exhibits increased water solubility compared with unfunctionalised graphene. Similarly, amino-functionalised graphene shows a higher hydrophilicity when compared with nitro graphene and unfunctionalised graphene. Moreover, as a weak base, amino-graphene can be protonated at low pH, thereby yielding a positively charged graphene material. Thio-graphene can be useful to introduce structure-stabilising disulphide bonds in a species to which it is complexed, which are known to be readily cleavable under reducing conditions. Perhaps most importantly, the versatility of —$NO_2$, —$NH_2$, —$SO_3H$, halide, —$N_3$, —MgBr and —SH functional groups means that they can be readily converted into other functionalities.

It will be appreciated that the functional group —$SO_3H$ may be synonymously referred to throughout this document as "sulpho graphene" or "graphene sulphonate". It will also be understood that the functional groups forming part of the invention may be present in ionised form (e.g. —$SO_3^-$, —$NH_4^+$, and other intermediate degrees of ionisation).

In an embodiment, the functionalised graphene consists essentially of at least one functional group covalently bonded directly to an edge of a graphene plane, wherein the functional group is only selected from the group consisting of —$NO_2$, —$NH_2$, —$SO_3H$, halide, —$N_3$, —MgBr and —SH, and wherein the functional group is only bound to an edge of the graphene plane.

In another embodiment, the functionalised graphene consists of at least one functional group covalently bonded directly to an edge of a graphene plane, wherein the functional group is only selected from the group consisting of —$NO_2$, —$NH_2$, —$SO_3H$, halide, —$N_3$, —MgBr and —SH, and wherein the functional group is only bound to an edge of the graphene plane.

In an embodiment, the functional group is selected from the group consisting of —$NO_2$, —$NH_2$, —$SO_3H$, —Br, —$N_3$, —MgBr and —SH.

In another embodiment, the functional group is selected from the group consisting of —$NO_2$, —$NH_2$, —$SO_3H$ and —SH.

In an embodiment, the edge of the graphene to which the functional group is bound defines the periphery of the graphene.

In another embodiment, the edge of the graphene to which the functional group is bound defines a defect, break, void or other inconsistency within the hexagonal arrangement or threefold symmetry of the graphene plane.

In another embodiment, the graphene comprises a plurality of functional groups. The extent to which the graphene is functionalised may be dependent on the characteristics, such as solubility and wettability, which the functionalised graphene should ideally possess.

In another embodiment, the at least one functional group is exchangeable for another functional group (e.g. —Br is exchangeable for —$N_3$).

In another embodiment, the plurality of functional groups are different. From the perspective of future applications or synthesis use, it may be desirable for graphene to be functionalised with a varying extent with a plurality of different functional groups. The plurality of different functional groups may be arranged in an orthogonal manner. Suitably, the plurality of functional groups are identical.

In another embodiment, the functionalised graphene is in solution or in a suspension.

In another embodiment, the functionalised graphene is attached to a solid support. Suitably, the solid support is a Si wafer coated with $SiO_2$.

In another aspect, the present invention provides functionalised graphene obtainable, obtained or directly obtained by any process for preparing edge functionalised graphene described herein.

Process for Preparation of Functionalised Graphene

As described hereinbefore, in a second aspect the present invention provides a process for the preparation of functionalised graphene comprising at least one functional group covalently bonded directly to an edge of a graphene plane, the functional group being selected from the group consisting of —$NO_2$, —$NH_2$, —$SO_3H$, halide, —$N_3$, —MgBr and —SH, the process comprising the steps of:
  a) preparing a sample of graphene to be functionalised,
  b) contacting the graphene with one or more reagents suitable for introducing at least one functional group selected from the group consisting of —$NO_2$, —$NH_2$, —$SO_3H$, halide, —$N_3$, —MgBr and —SH to any available edge of the sample of graphene, and
  c) isolating the functionalised graphene bearing only the at least one functional group selected from the group consisting of —$NO_2$, —$NH_2$, —$SO_3H$, halide, —$N_3$, —MgBr and —SH.

The process for the preparation of functionalised graphene in accordance with the present invention presents a number of advantages over prior art processes. Principally, the process of the present invention proceeds via a mechanism exhibiting a high degree of selectivity. Specifically, when applied to a sheet of graphene, the process of the present invention, which in certain embodiments proceeds via electrophilic aromatic substitution, results in only an edge of the graphene plane, where a hydrogen atom is situated, becoming functionalised. The edge may define the periphery of the graphene being functionalised, or a defect, void or other inconsistency within the two-dimensional graphene plane. When compared with prior art processes, the topological specificity of the present process allows graphene's desirable characteristics stemming from its two-dimensional structure, including its electronic properties, to be preserved.

In addition to the above, the process of the invention presents a number of advantages over prior art ball-milling techniques, in which graphite is mechanically exfoliated and then functionalised in-situ during the milling process. In particular, due to the fact that mechanical exfoliation and functionalization are conducted in parallel, such techniques afford little to no control over the size of the resulting edge-functionalised graphene flakes. For example, such techniques are likely to give rise to a sample of functionalised graphene having a wide size distribution. Similarly, the high-energy nature of such techniques translates to a lack of control over the exact nature of the functional group being introduced to graphene, for example, mechanically fractured C—C bonds that are not functionalised in the manner intended are then susceptible to reaction with atmospheric moisture or oxygen, which results in graphene that has been modified with a variety of unwanted functional groups. Similarly, ball-milling graphite under a nitrogen atmosphere was found to give rise to flakes having a mixture (and hence a lack of control) of pyrazolic and pyridizinic groups[15]. In contrast to this, the process of the present invention allows for the controlled introduction of predetermined quantities of specific functional groups of interest and creating products with dimensions close to those of the starting graphene. In addition, such ball-milling techniques should predominantly functionalise at the sites of mechanically fractured C—C bonds, whereas the functionalization process of the invention may be performed at any available edge of the graphene sample.

Furthermore, the process of the present invention represents an improvement on prior art methods, such as those involving Friedel-Crafts alkylations and acylations, since the heteroatoms of the functional groups are bound directly to the edge of the graphene plane. Moreover, direct linking of the functional group to the graphene plane improves electron transport between the graphene sheet and moieties bonded thereto through the functionality. Aside from the above-discussed advantages, depending on the nature of the functional group bound to the graphene, the solubility of graphene in solution, or the wettability properties of graphene-coated surfaces, can be tailored according to a particular application or further synthetic process.

In an embodiment, step b) comprises contacting the graphene with one or more reagents suitable for introducing at least one functional group selected from the group consisting of —$NO_2$, —$NH_2$, —$SO_3H$ and —SH.

In an embodiment, the graphene prepared in step a) is in solution, in suspension, or attached to a solid support. It will, however, be understood that step a) may simply involve providing a sample of pre-formed graphene and then preparing it for functionalization step b) (e.g. by dispersing the graphene in a suitable reaction medium).

Suitably, the graphene is prepared by exfoliation of graphite. In an embodiment, the graphene is prepared by mechanical exfoliation of graphite, for example by the Scotch tape method. The mechanically exfoliated graphene may be disposed on a Si wafer coated with $SiO_2$ prior to step b). In another embodiment, the graphene is prepared by sonicating graphite in a solvent. More suitably, the exfoliation comprises sonicating the graphite in N-methyl-2-pyrrolidone or N,N-dimethylformamide.

Suitably, the graphene is prepared by chemical vapour deposition (CVD). More suitably, the graphene is prepared by chemical vapour deposition and then transferred to a Si wafer coated with $SiO_2$.

In an embodiment, the functionalised graphene is isolated in step c) by a filtration route, comprising separating the functionalised graphene from one or more residual reagents by a filtration, followed by resuspending the isolated functionalised graphene. Suitably, the filtration route comprises separating the functionalised graphene from one or more residual reagents by filtration using a nanoporous membrane. Suitably, if a dry powder is required, the filtration route further comprises lyophilising the suspended solution to a dry powder. Suitably, the filtration route is used when the functionalised graphene is produced from graphene prepared via exfoliation of graphite.

In another embodiment, the functionalised graphene is isolated in step c) by a washing route, comprising washing the functionalised graphene with at least one solvent, followed by drying the functionalised graphene. Suitably, the washing route comprises drying the functionalised graphene in a stream of inert gas, or using a vacuum desiccator. More suitably, the inert gas is nitrogen gas. Suitably, the washing route is used when the functionalised graphene is produced from graphene prepared via chemical vapour deposition.

In another embodiment, the functionalised graphene is isolated in step c) by affinity chromatography.

In an embodiment, where step b) comprises contacting the graphene with more than one reagent, said reagents may be introduced simultaneously or sequentially.

In a particular embodiment, in step b), the graphene is contacted with one or more nitrating reagents to introduce —$NO_2$ groups on the edge of the graphene. Suitably, the one or more nitrating reagents are concentrated nitric acid and concentrated sulphuric acid. Suitably, the concentrated nitric acid and concentrated sulphuric acid are cooled over ice. Suitably, following contact with the one or more nitrating reagents, the graphene is contacted with a neutralising reagent. More suitably, the neutralising reagent is sodium hydroxide.

In another particular embodiment, following the introduction of —$NO_2$ groups on the edge of the graphene, step b) further comprises a step of contacting the nitrated graphene with a reducing agent to reduce the —$NO_2$ groups to —$NH_2$ groups. Suitably, the reducing agent is Raney nickel and formic acid. Alternatively, the —$NO_2$ groups on the edge of the graphene are electrochemically reduced to —$NH_2$ groups.

In another particular embodiment, in step b), the graphene is contacted with one or more sulphonating agents to introduce —$SO_3H$ groups onto the edge of the graphene. Suitably, the one or more sulphonating reagents are chlorosulphonic acid followed by sodium hydroxide.

In another particular embodiment, following the introduction of —$SO_3H$ groups on the edge of the graphene, step b) further comprises contacting the sulphonated graphene with a reducing agent to reduce the —$SO_3H$ groups to —SH groups. Suitably, the reducing agent is triphenylphosphine and iodine. Suitably, the step of contacting the sulphonated graphene with a reducing agent is conducted under an inert atmosphere, such as, for example, nitrogen.

Suitably, step b) is carried out over a period of 0.1-48 hours.

Graphene Conjugates

As described hereinbefore, in a third aspect the present invention provides a graphene conjugate comprising at least one organic or inorganic moiety covalently attached to the at least one functional group of the functionalised graphene defined herein.

As described hereinbefore, in a fourth aspect, the present invention provides a graphene conjugate, wherein the graphene conjugate is formed by reaction of at least one organic or inorganic moiety with the at least one functional group of the functionalised graphene as defined herein.

The graphene conjugates of the present invention allow the interesting and desirable properties of graphene to be exploited in a wide variety of applications. The —$NO_2$, —$NH_2$, —$SO_3H$, halide, —$N_3$, —MgBr and —SH functional groups located on an edge of the graphene plane react readily with an array of organic and inorganic moieties in a manner that does not compromise the two-dimensional structure of the graphene plane, thereby preserving graphene's interesting characteristics and allowing them to be advantageously exploited in a particular end application. Depending on the chemical nature of the functional group, portions of the functional group may or may not form part of the graphene conjugate. The properties of graphene may be useful in a variety of fields, including separation technologies, composites/material science and biological or in vivo applications including sensing, drug delivery, therapeutics, tractography, imaging, and labelling.

In one embodiment, when at least one functional group is $NO_2$, —$NH_2$, —$SO_3H$ or —SH, at least a portion of functional group forms part of the graphene conjugate.

In one embodiment, the at least one organic or inorganic moiety is covalently attached via a coupling reaction between the organic or inorganic moiety (or a precursor thereof), and the at least one functional group.

In another embodiment, the at least one organic or inorganic moiety is selected from the group consisting of amino acids, proteins, antibodies, carbohydrates, polymers, nanoparticles, metals, chelators, nucleic acids, oligonucleotides, aptamers, fluorophores, metal oxides, biologically active compounds or biomarkers. In another embodiment, the at least one organic or inorganic moiety is a chelator. Edge-modified graphene directly coupled to a chelator for metal ion or metal may find use in end applications such as metal sequestration and recovery. For example, a chelator graphene may be added to a mixture of metal ions. Chelators selectively bind target metal ions to remove them from the mixture. The graphene-chelator complex can then be removed by filtration. The metal can be released electrochemically, and the graphene reused. Chelators that fluoresce (e.g., chelated lanthanides) highlight edge regions (including defects in the basal plane, i.e., internal edges) and are useful for quantifying defects that will impede carrier mobility. Chelated metals on graphene can also be used for medical imaging. Examples of chelated metals for this purpose include, but are not limited to, indium-111 in diethylene triamine pentaacetic acid (DTPA) for single-photon emission computed tomography and gadolinium(III) in 1,4,7,10-tetraazacyclododecane-1,4,7,10-tetraacetic acid (DOTA) in MRI imaging. Edge-modified graphene linked to chelators such as these may be used to follow the distribution of graphene in biology, or may be used as a proxy for the position of agents such as drug molecules that are loaded on the basal plane of the graphene.

In another embodiment, the at least one organic or inorganic moiety is a metal. Optionally, the metal moiety may be bound to the graphene plane via a —Br functional group, so as to form a Grignard reagent.

In a particular embodiment, the at least one organic or inorganic moiety is a gold nanoparticle. Such a gold-graphene conjugate may be used in conjunction with scanning electron microscopy to demonstrate the edge-specificity of the functionalised graphene.

In another particular embodiment, the at least one organic or inorganic moiety is a mono-, di- or polysaccharide. By introducing biologically-active moieties, the biological activity of graphene in a number of scenarios can be determined. Suitably, the mono-, di- or polysaccharide is allyl mannoside. The resulting "glyco graphene" exhibits a high degree of water solubility, which is highly desirable for applications requiring the use of graphene under physiological conditions. Moreover, such a graphene conjugate can be used to immobilise mannose-specific glycan-binding proteins, such as concanavalin A (ConA). This ability to introduce ligands for specific proteins could be exploited in cancer biomarker systems, where cell-surface carbohydrates and their corresponding glycan-binding proteins continue to attract interest.

Process for Preparation of a Graphene Conjugate

As described hereinbefore, in a fifth aspect the present invention provides a process for the preparation of a graphene conjugate as defined hereinbefore, the process comprising the steps of:
a) preparing a sample of functionalised graphene in accordance with a process defined hereinbefore,
b) reacting the functionalised graphene with at least one organic or inorganic moiety such that the organic or inorganic moiety is covalently attached to the graphene via one or more of the functional groups present on the functionalised graphene, and
c) isolating the graphene.

The process for the preparation of a graphene conjugate in accordance with the present invention permits graphene to be modified in a manner which allows its interesting and desirable properties to be exploited in a wide variety of applications. The —NO$_2$, —NH$_2$, —SO$_3$H and —SH functional groups located on an edge of the graphene plane can be made to react readily with an array of organic and inorganic moieties in a manner that does not compromise the two-dimensional structure of the graphene plane, thereby preserving graphene's interesting characteristics and allowing them to be advantageously exploited in a particular end application. The properties of graphene may be useful in a variety of fields, including separation technologies, and biological or in vivo applications including sensing, drug delivery, therapeutics, tractography, imaging, composites/material science and labelling.

The reactivity of —NO$_2$, —NH$_2$, —SO$_3$H and —SH functional groups is well documented in the literature, and the skilled person will readily understand how the functionalised graphene may be decorated with various organic and inorganic moieties.

In an embodiment, step b) is performed in at least one aqueous or organic solvent.

In another embodiment, step b) is performed over a period of 0.1-48 hours.

In another embodiment, step c) comprises separating the graphene conjugate from one or more residual reagents, followed by washing the separated graphene conjugate with at least one solvent.

In another embodiment, step c) comprises separating the graphene conjugate by filtration. Filtration is suitably used when the graphene conjugate is in solution. Optionally, the filtered graphene conjugate is then redispersed in solution by sonication.

In another embodiment, step c) further comprises the step of drying the washed functionalised graphene conjugate in a stream of inert gas, such as nitrogen, or in a vacuum desiccator. Such a protocol is suitably used when the graphene conjugate is provided as a surface layer on a solid support.

In a particular embodiment, step b) comprises contacting the functionalised graphene with gold nanoparticles. The resulting gold-graphene conjugate may be used in conjunction with scanning electron microscopy to demonstrate the edge-specificity of the functionalised graphene.

In another particular embodiment, step b) comprises contacting the functionalised graphene with a mono-, di- or polysaccharide. By introducing biologically-active moieties, the biological activity of graphene in a number of scenarios can be determined. Suitably, the mono-, di- or polysaccharide is allyl mannoside. The resulting "glyco graphene" exhibits a high degree of water solubility, which is highly desirable for applications requiring the use of graphene under physiological conditions. Moreover, such a graphene conjugate can be used to immobilise mannose-specific glycan-binding proteins, such as concanavalin A (ConA). This ability to introduce ligands for specific proteins could be exploited in cancer biomarker systems, where cell-surface carbohydrates and their corresponding glycan-binding proteins continue to attract interest.

In another embodiment, the inorganic moiety is a functionalised support material, the support material being suitable for use in column chromatography. Suitably, the support material is either composed of metal oxides, including silica, alumina and titania, or is coated with such materials. Suitably, the support material is modified with an organosilane modifier having the general formula $RSiX_1X_2X_3$, where R is a functional moiety intended for reaction with the edge functionalised graphene, and $X_1$, $X_2$ and $X_3$ are each independently ethoxy, methoxy, hydroxyl, chloro, hydrido or alkyl. R may contain a functional group selected from allyl, carboxylic acid, amino, alkynyl, azido, isothiocyanato, carbonyl, epoxy and glycidoxy. Such support materials can be modified by hydrolysing and reacting them with the modifying agent, typically by mixing with an alcohol solvent in the presence of a controlled amount of water and a small amount of acid or base catalyst. The materials can be separated by filtration or centrifugation. Edge functionalised graphene is then mixed with the modified support material using established protocols for bioconjugation.

Examples of suitable support material modifiers include: 3-(N-allylamino)propyltrimethoxysilane, allyldichlorosilane, allyldimethoxysilane, allyloctadecylmethylsilane, O-allyloxy(polyethyleneoxy)trimethylsilane, 11-allyloxyundecyltrimethoxysilane, allylmethyldimethoxysilane, allyltrichlorosilane, allyltriethoxysilane, allyltrimethoxysilane, diallyldichlorosilane, mercaptomethyl)methyldiethoxysilane, 3-mercaptopropylmethyldimethoxysilane, 3-mercaptopropyltriethoxysilane, 3-mercaptopropyltrimethoxysilane, 11-mercaptoundecyltrimethoxysilane, 4-aminobutyltriethoxysilane, 4-amino-3,3-dimethylbutylmethyldimethoxysilane, 4-amino-3,3-dimethylbutyltrimethoxysilane, N-(2-aminoethyl)-3-aminoisobutylmethyldimethoxysilane, (aminoethylaminomethyl)phenethyltrimethoxysilane, N-(2-aminoethyl)-3-aminopropylmethyldiethoxysilane, N-(2-aminoethyl)-3-aminopropylmethyldimethoxysilane, N-(2-aminoethyl)-3-aminopropylsilanetriol, N-(2-aminoethyl)-3-aminopropyltriethoxysilane, N-(2-aminoethyl)-3-aminopropyltrimethoxysilane, N-(6-aminohexyl)aminomethyltriethoxysilane, N-(6-aminohexyl)aminopropyltrimethoxysilane, N-(2-aminoethyl)-11-aminoundecyltrimethoxysilane, 3-(m-aminophenoxy)propyltrimethoxysilane, m-aminophenyltrimethoxysilane, p-aminophenyltrimethoxysilane, aminophenyltrimethoxysilane, N-3-[(amino(polypropyleneoxy)]aminopropyltrimethoxysilane, 3-aminopropylmethyldiethoxysilane, 3-aminopropylsilanetriol, 3-aminopropyltriethoxysilane, 3-am inopropyltrimethoxysilane, 11-aminoundecyltriethoxysilane, 3-azidopropyltriethoxysilane, 11-azidoundecyltrimethoxysilane, 2-(3,4-epoxycyclohexyl)ethylmethyldiethoxysilane, 2-(3,4-epoxycyclohexyl)ethyltriethoxysilane, 2-(3,4-epoxycyclohexyl)ethyltrimethoxysilane, 5,6-epoxyhexyltriethoxysilane, (3-glycidoxypropyl)dimethylethoxysilane, (3-glycidoxypropyl)methyldiethoxysilane, (3-glycidoxypropyl)methyldimethoxysilane, 1-(3-glycidoxypropyl)-1,1,3,3,3-pentaethoxy-1,3-disilapropane, (3-glycidoxypropyl)triethoxysilane, and (3-glycidoxypropyl)trimethoxysilane.

Alternatively, the organic or inorganic moiety is a polymeric support material, including those made of biological and synthetic polymers and co-polymer including but not limited to polystyrene, polymethylmethacrylate, polycarbonate, siliceous, polyethylene oxide, polysaccharides and polypeptides. The polymeric supports may be cross-linked, and may contain inherent functional moieties suitable for reaction with edge functionalised graphene, or such functional moieties may be introduced into the polymeric support by grafting.

Edge-functionalised graphene conjugated to support materials may find utility in applications where it is desirable to separate graphene flakes based on their size.

Use of a Graphene Conjugate

As described hereinbefore, in a sixth aspect the present invention provides a use of functionalised graphene defined herein or a graphene conjugate defined herein for identifying defects present in the graphene plane. Given that many of graphene's desirable properties stem from its unique structure, it would be advantageous to be able to determine the extent to which the structure is free from imperfections. Moreover, given that graphene manufacturing protocols are still in a state of infancy, it has become necessary to develop suitable quality control techniques. Owing to the edge-specificity of the graphene conjugates disclosed herein, the detection of one or more conjugated moieties within the graphene plane is indicative of a defect, break, void or other inconsistency within the hexagonal arrangement or threefold symmetry of the graphene plane. The graphene conjugates of the present invention therefore provide a means for determining the quality of a graphene sample, both in terms of the number of imperfections present, and their location within the sample.

In one embodiment, the graphene conjugate comprises a conjugated moiety that is fluorescent. Suitably, the graphene conjugate comprises a conjugated moiety that is a fluorophore. Any suitable fluorophore may be used. Suitably, the fluorophore is selected from the group consisting of fluorescein-5-EX, green fluorescent protein, FITC-labelled Concanavalin A, and fluorescent quantum dots.

EXAMPLES

Materials and Equipment

All chemicals were purchased and used without further purification. Primary amines were detected on Merck silica TLC plates with ninhydrin solution (300 mg ninhydrin, dissolved in 100 mL butanol and 3 mL conc. acetic acid), followed by heat treatment. Sulphhydryl groups were detected using Ellman's reagent: 39.6 mg 5,5'-dithio-bis-[2-nitrobenzoic acid] (Ellman's reagent) were dissolved in 10 mL PBS (pH 7.4) and the solution was used immediately.

Attenuated total reflectance (ATR) FTIR spectra were recorded on a Thermo Nicolet Nexus 5700 FT IR Spectrometer with a Smart Orbit ATR unit Diamond 30000-200 $cm^{-1}$.

Scanning electron microscopy images were acquired using an FEI Quanta 650 FEG-SEM operating at 3-4 kV. CVD graphene samples on SiO2/Si were mounted on 12.5 mm aluminum stubs. No surface coatings were applied.

Fluorescence images were collected on a BX51 upright microscope using UPlanFLN objectives and captured using a Coolsnap camera (Photometrics) through MetaVue Software (Molecular Devices). A specific band pass filter set for FITC (Ex. BP480/40, Dichroic Q505LP, Em. 535/50) was used.

Raman spectra were recorded on a Renishaw RM System 1000 Mk1 spectrometer with 633 nm (1.96 eV) illumination. To compensate for drifts in the calibration to Si (520 $cm^{-1}$), the Raman shift was offset, typically by ±2 $cm^{-1}$, by fixing the energy of the G peak to 1581 $cm^{-1}$. The shift of the G peak is insensitive to the number of layers of graphene.

Thermogravimetric analyses (TGA) were collected from a TA Instruments Q500. Samples of ca. 3 mg were heated at 10° C. $min^{-1}$ in a nitrogen atmosphere.

Example 1—Preparation of Functionalised Graphene in Solution

Preparation of Pristine Graphene Solution

Graphene solutions were prepared from natural graphite flakes (Branwell Graphite, Ltd Grade 2369). Following the method of Coleman[16], 2 g graphite were sonicated in 500 mL N-methyl-2-pyrrolidone (NMP) at 37/100 Hz for 48 h. Remaining graphite was removed by centrifugation (3×20 min at 4000 rpm). The supernatant was a stable graphene dispersion (ca. 0.4 g $L^{-1}$). Graphene reaction solutions were vacuum filtered through 0.02 μm Whatman Anodisc membrane filters to create graphene laminates. For analysis, samples were dried as laminates on the filter membrane or re-dispersed in water by sonication and freeze-dried. For long term storage the samples were kept in a desiccator at room temperature.

Synthesis of Nitro Graphene Solution 20 mL 100% nitric acid and 28 mL concentrated sulphuric acid were carefully mixed and cooled with ice. 75 ml graphene solution in NMP were added in drops, while the ice was allowed to thaw. The mixture is stirred overnight, poured on 200 mL ice, filtered and washed with 700 mL water until the filtrate was pH neutral. The filter was transferred in a round bottom flask and the nitro graphene sonicated in 75 mL NMP.

Synthesis of Amino Graphene Solution 20 mL of nitro graphene were mixed with 7 mL of Raney-Ni suspension in water. 20 mL formic acid were added and the mixture was stirred for 20 h. Decanting several times with the help of a strong magnet facilitated the removal of the catalyst. The remaining mixture was filtered and washed with 500 mL concentrated sodium hydroxide solution, 500 mL water and 500 mL ethanol. The product was sonicated in 20 mL water and kept in solution until further use.

Synthesis of Chlorosulphonate Graphene Solution

Mix 100 ml graphene solution and 10 ml chlorosulphonic acid in a round bottom flask. Heat the mixture to 55° C. under stirring. Leave to react overnight. Pour the mixture in ice and add sodium hydroxide to bring the pH up to 10. Leave to react for 30 min at room temperature (mixture turns yellow). Neutralise and filter (alkaline solution dissolves the Anodisc). Wash with water. Re-sonicate into water and freeze dry.

Synthesis of Sulpho Graphene Solution 15 g sodium hydroxide was dissolved in 19.5 mL of chlorosulphonated graphene in water and the mixture was sonicated for 2 h. The product war filtered and washed with water until the filtrate was neutral. Sulpho graphene was re-dispersed in water by sonication and freeze dried in aliquots.

Synthesis of Thio Graphene Solution

Dry sulpho graphene (freeze dried from 12 ml of sulpho graphene in water) was suspended in anhydrous benzene by sonication in a $N_2$-atmosphere. 4.6 g (10 mmol) triphenylphosphine and 300 mg (0.6 mmol) iodine were added and the mixture was stirred under a $N_2$ atmosphere at 90° C. for 21 h. The product was washed with 500 mL toluene, 200 mL acetone, 100 ml sodium thiosulphate solution and 1000 mL water. Thio graphene was re-dispersed in 12 mL water by sonication.

Example 2—Preparation of CVD Functionalised Graphene

Pristine Graphene Films

Uniform polycrystalline films of graphene were grown by chemical vapour deposition (referred to as CVD graphene) and transferred to Si wafers with a surface layer of thermally grown oxide (2-DTech, Ltd).

Synthesis of CVD Nitro Graphene 5 mL 100% nitric acid and 7 mL concentrated sulphuric acid were carefully mixed in a glass vial cooled with ice. A CVD graphene sample was added to the glass vial and left to react overnight. The sample was rinsed with dilute sodium hydroxide solution, water and acetone, was dried in a nitrogen gas stream and stored at room temperature.

Synthesis of CVD Amino Graphene

To 1.5 mL of an aqueous suspension of Raney Ni in a glass vial 8 mL formic acid were added slowly. A CVD nitro graphene sample was transferred to the vial and left to react overnight. The sample was rinsed with water and acetone, was dried in a nitrogen gas stream and stored at room temperature.

Synthesis of CVD Chlorosulpho Graphene 8 mL anhydrous DMF and 2 mL chlorosulphonic acid were mixed in a glass vial. The CVD graphene sample was left to react in the mixture overnight. The CVD graphene sample was rinsed with acetone and water and transferred immediately into the next reaction vial for hydrolysis of the chlorosulphonates.

Synthesis of CVD Sulpho Graphene

A sodium hydroxide solution, pH 10 was prepared and 10 mL were transferred to a glass vial. The chlorosulphonated CVD graphene sample was left in the sodium hydroxide solution for 15 min and rinsed immediately with water and acetone. The sample was dried in a nitrogen gas stream and stored at room temperature.

Synthesis of CVD Thio Graphene 4.6 g (10 mmol) triphenylphosphine were dissolved in anhydrous toluene and heated up to 90° C. 300 mg (0.6 mmol) iodine were added under stirring. The stirrer was stopped, the flask was opened keeping a strong nitrogen counter flow and the sulphonated CVD graphene sample was added. The mixture was kept in a nitrogen atmosphere and heated to 90° C. overnight. The CVD graphene sample was rinsed with acetone, water and ethanol, dried in a nitrogen gas stream and stored at room temperature.

Example 3—Preparation of Graphene Conjugate in Solution

Synthesis of Allyl α-D-Mannopyranoside Solution by Fischer Glycosylation

According to a literature protocol[17], Allyl alcohol (125 mL, 1.84 mol) was cooled to 0° C., acetyl chloride (10 mL, 14.0 mmol) was added in drops, and the mixture was stirred at 0° C. for 1 h. After heating to 70° C., mannose (10.0 g, 55.6 mmol) was added and the reaction was stirred under reflux for 5 h. It was neutralized with sodium hydrogen carbonate and filtrated. After three co-distillations with toluene, the solvent was removed and the crude product was purified by flash column chromatography on silica (EtOAc/MeOH, 8:2).

Synthesis of Glyco Graphene Solution

To 12 mL of thio graphene in water 200 mg (909 μmol) allyl mannoside and 1 spatula benzoyl peroxide were added and the mixture was stirred at 65° C. for 21 h. The mixture was filtered and washed with ethanol, dichloromethane, ethanol and water and re-dispersed in 15 mL water by sonication.

Synthesis of Graphene with Covalently Attached Metal Ion Chelators 48 mg $Ln(OTf)_3$ (Ln=Yb,Eu,Tb) was added to 30 mg Allyl DO3A in 0.5 mL methanol. The reaction was left to react at 50° C., overnight.

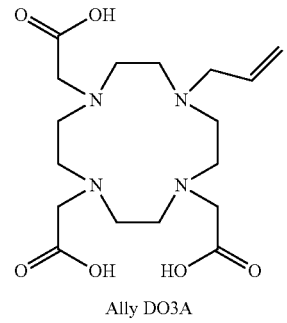 [SMILES: C=CCN1CCN(CC(=O)O)CCN(CC(=O)O)CCN(CC(=O)O)CC1]

Ally DO3A

Allyl DO3A (with lanthanide ion inserted) was added to 2 mL 0.4 mg mL$^{-1}$ thiolated graphene to get it to a concentration of 1 mM. A spatula of benzoyl peroxide was added and the reaction heated to 55° C. overnight. The reaction was then quenched with sodium sulfite and the solution filtered and resuspended in methanol.

Example 4—Preparation of CVD Graphene Conjugate

Synthesis of CVD Glyco Graphene 150 mg (682 μmol) allyl mannoside and 1 spatula benzoyl peroxide were dissolved in ethanol. A CVD thio graphene sample was added to the reaction vial and the mixture was heated to 65° C. overnight. The CVD graphene sample was rinsed with ethanol, water and acetone, dried in a nitrogen gas stream and stored at room temperature.

Binding of Gold Nanoparticles to CVD Thio Graphene

Gold nanoparticles (20 nm diameter in 0.1M phosphate-buffered saline, ~6×10$^{11}$ particles ml$^{-1}$, Aldrich) were diluted in PBS to a final concentration of 10 µM. 10 mL of this suspension were transferred to a glass vial. A sample of CVD thio graphene (or CVD sulpho graphene as a negative control) was immersed in the nanoparticle suspension overnight at room temperature. The sample was rinsed with water and acetone and dried in a nitrogen gas stream and stored at room temperature.

Example 5—ConA Binding to CVD Glycol Graphene

FITC-ConA was dissolved in binding buffer (20 mM Tris, 500 mM NaCl, 1 mM CaCl$_2$, 1 mM MgCl$_2$, pH 7.2) in a glass vial wrapped in aluminum foil. The CVD glyco graphene sample was added to the vial incubated at 37° C. for 2 h. The CVD graphene sample was rinsed with water, dried in a nitrogen gas stream and examined under a fluorescence microscope.

Example 6—Characterisation Studies

Attenuated Total Reflectance FT IR

Figure 2:
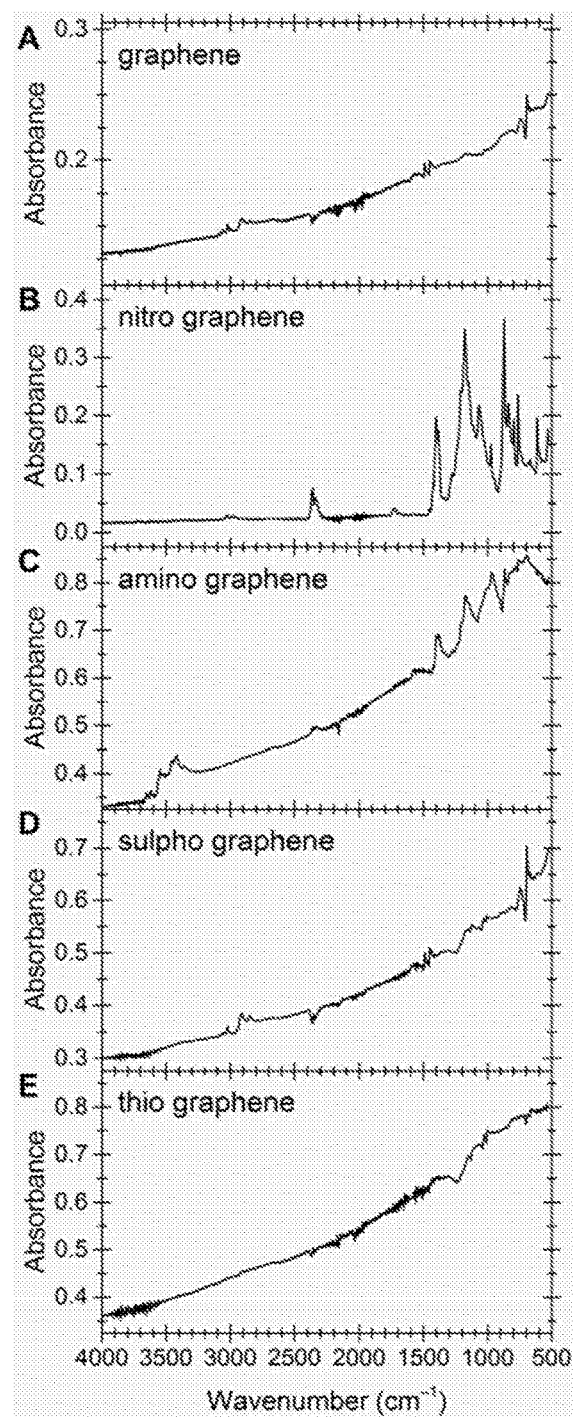
FIG. 2 shows ATR FT IR spectra of (A) unfunctionalised graphene; (B) nitro graphene; (C) amino graphene; (D) sulpho graphene; and (E) thio graphene.
Figure 3:
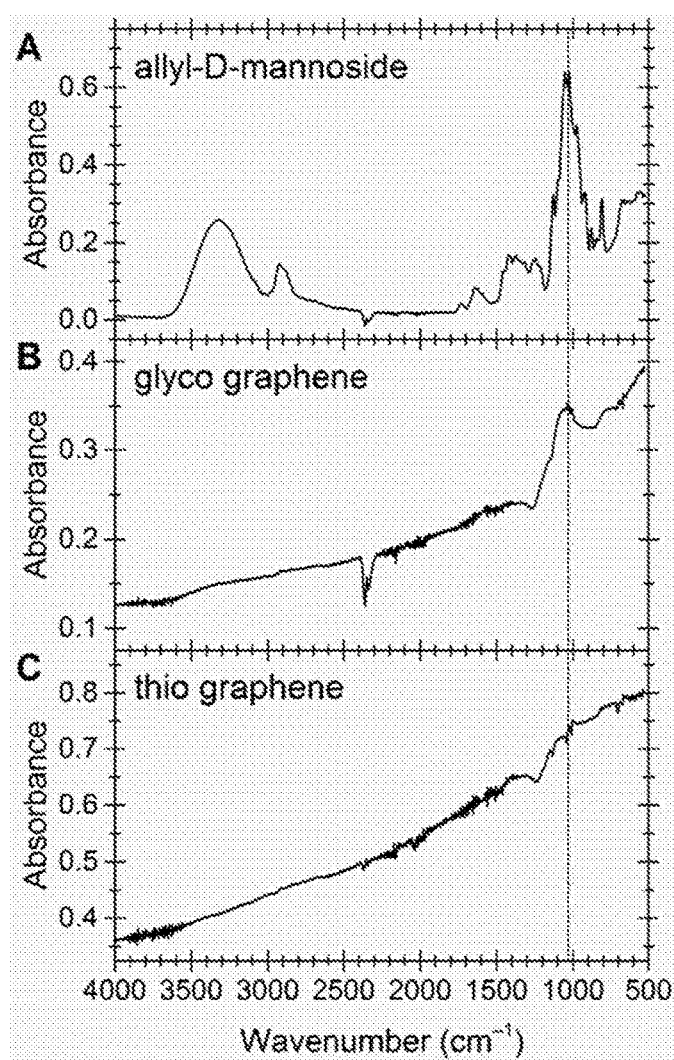
FIG. 3 shows ATR FT IR spectra of (A) allyl mannoside; (B) allyl mannoside-graphene ("glyco graphene"); and (C) thio graphene.

FIG. 2 shows ATR FT IR spectra of (A) unfunctionalised graphene; (B) nitro graphene; (C) amino graphene; (D) sulpho graphene; and (E) thio graphene. FIG. 3 shows ATR FT IR spectra of (A) allyl mannoside; (B) glyco graphene; and (C) thio graphene.

Raman Spectroscopy

Figure 4:
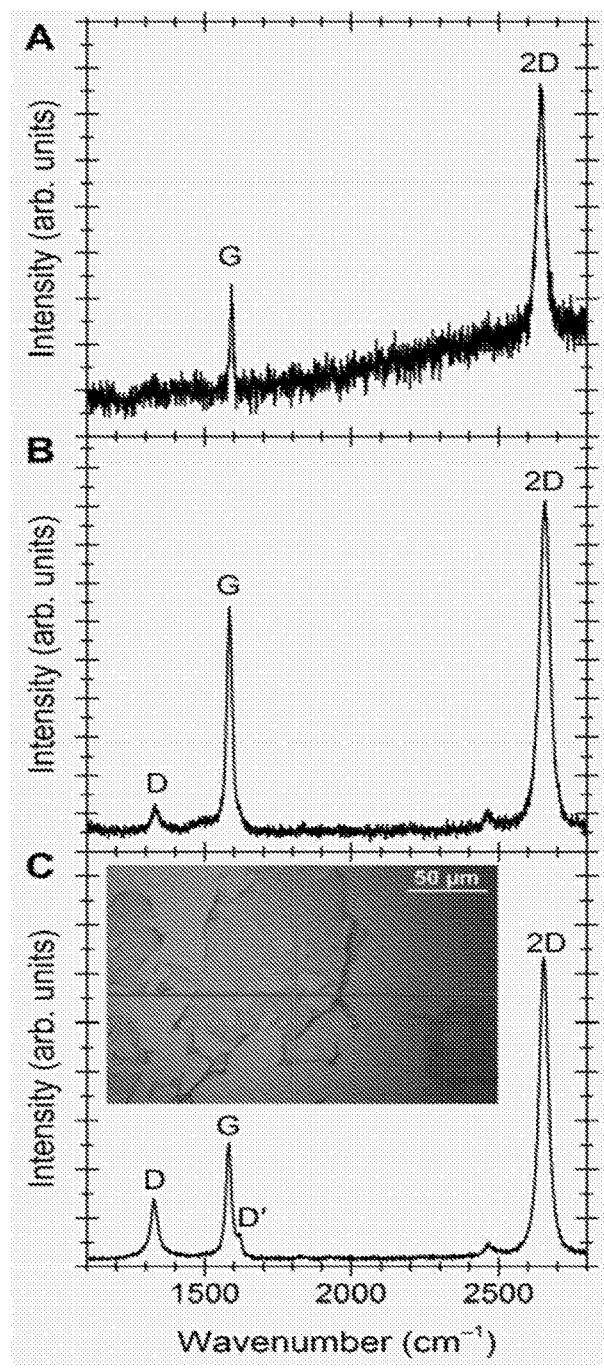
FIG. 4 shows Raman spectra of (A) unfunctionalised CVD graphene, spectrum taken at the centre of the sample; (B) unfunctionalised CVD graphene, spectrum taken at the edge of the sample; and (C) CVD thio graphene, spectrum taken at the crosshairs shown in the inset image.

FIG. 4 shows Raman spectroscopy spectra of (A) unfunctionalised CVD graphene, spectrum taken at the centre of the sample; (B) unfunctionalised CVD graphene, spectrum taken at the edge of the sample; and (C) CVD thio graphene, spectrum taken at the crosshairs shown in the inset image. The locations of the Ramen peaks shown in FIG. 4 are shown in Table 1 below. The position of the G peak was set to 1581 cm$^{-1}$.

TABLE 1

Locations of Raman peaks shown in FIG. 4

| Sample | D/cm$^{-1}$ | G/D ratio$^a$ | D'/cm$^{-1}$ | D" + D/cm$^{-1}$ | 2D/cm$^{-1}$ |
|---|---|---|---|---|---|
| (a) pristine CVD centre | n.d. | n.d. | n.d. | n.d. | 2631 |
| (b) pristine CVD edge | 1329 | 6.33 | 1620 | 2462 | 2656 |
| (c) thiolated CVD centre | 1326 | 1.89 | 1617 | 2468 | 2652 |

$^a$Based on counts above baseline after fitting peaks to Gaussian functions.

Thermogravimetric Analysis

Figure 5:
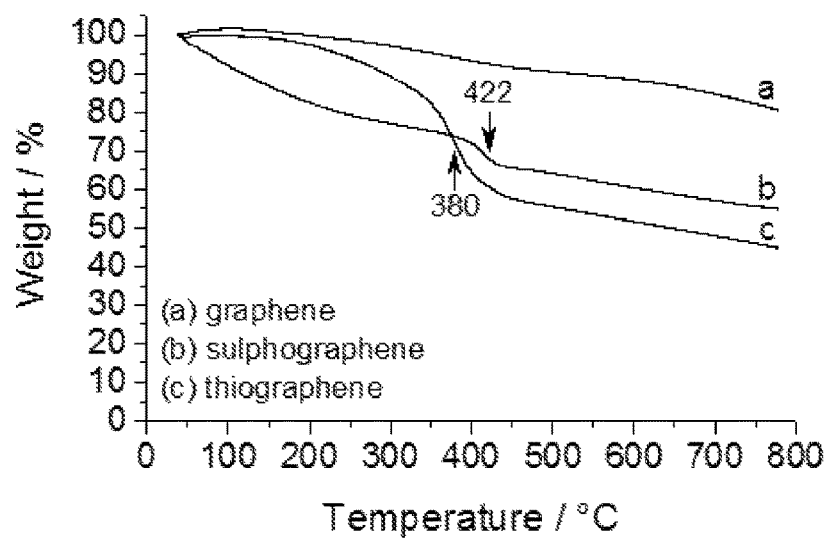
FIG. 5 shows TGA analysis of (A) unfunctionalised graphene, (B) sulpho graphene, (C) thio graphene, (D) amino graphene and (E) nitro graphene. All samples were prepared from graphene obtained via ultrasonic exfoliation.
Figure 5:
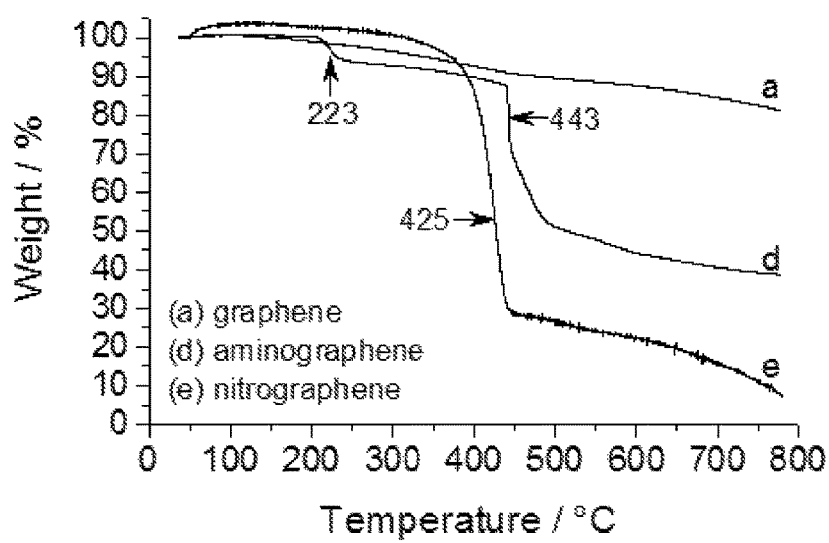

FIG. 5 shows TGA analysis of (A) unfunctionalised graphene, (B) sulpho graphene, (C) thio graphene, (D) amino graphene and (E) nitro graphene. All samples were prepared from graphene obtained via ultrasonic exfoliation. Each trace shows a transition temperature distinct from the others.

Wettability

Figure 6:
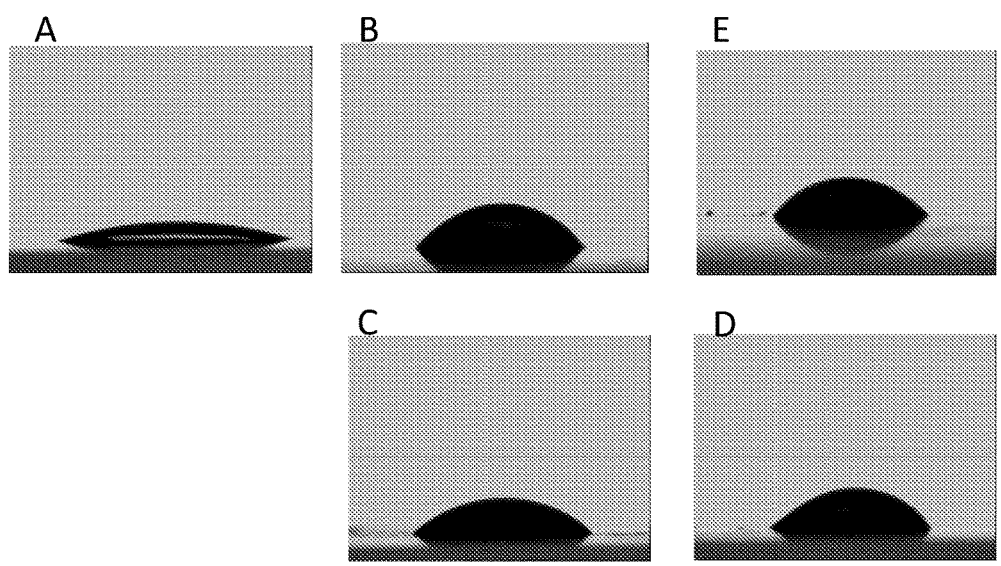
FIG. 6 shows contact angle measurements of water droplets on glass slides covered with (A) nothing; (B) unfunctionalised graphene; (C) sulpho graphene; (D) thio graphene; and (E) glyco graphene.

FIG. 6 shows contact angle measurements of water droplets on glass slides covered with (A) nothing; (B) unfunctionalised graphene; (C) sulpho graphene; (D) thio graphene; and (E) glyco graphene. FIGS. 6A-E therefore demonstrate tuneable wettability.

Solubility

Figure 7:
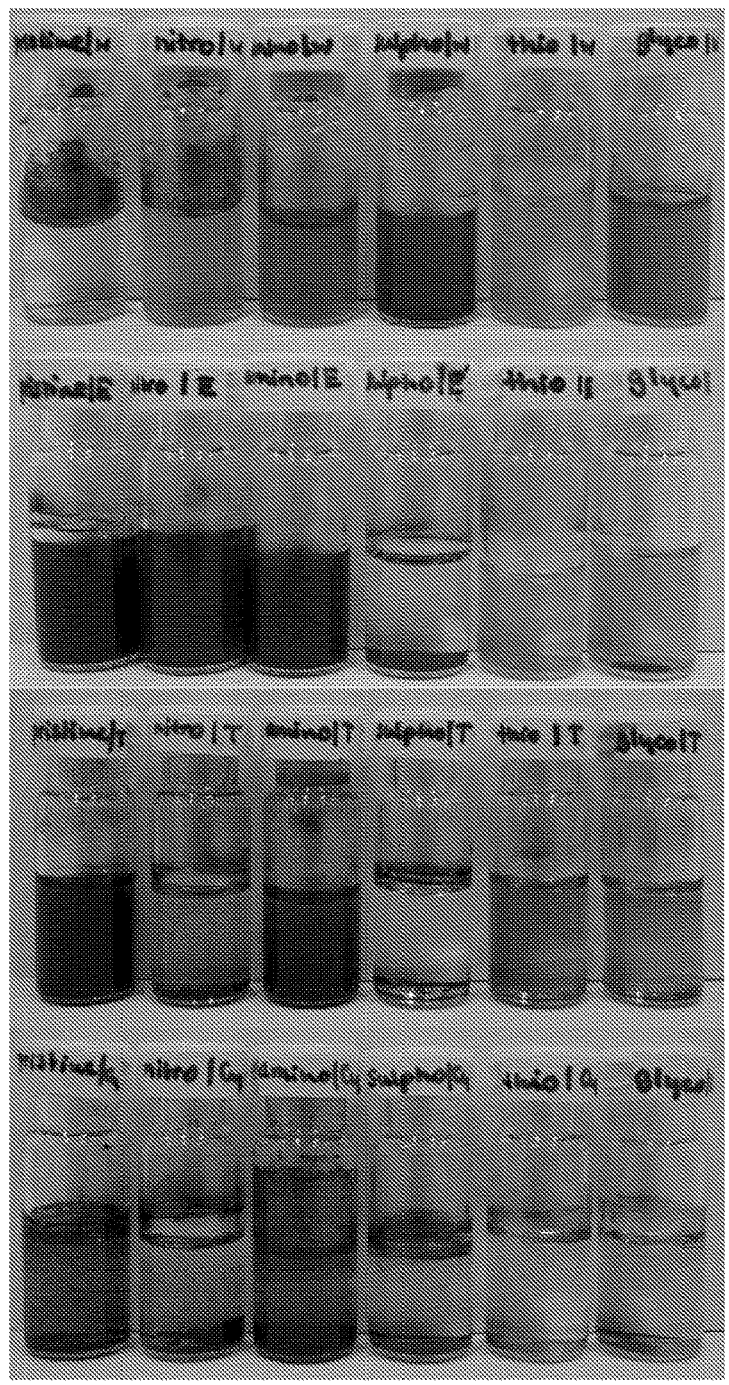
FIG. 7 shows the solubility of (left to right) unfunctionalised graphene, nitro graphene, amino graphene, sulpho graphene, thio graphene, and glyco graphene in (A) water; (B) ethanol; (C) toluene; and (D) cyclohexane.

FIG. 7 shows the solubility of (left to right) unfunctionalised graphene, nitro graphene, amino graphene, sulpho graphene, thio graphene, and glyco graphene in (A) water; (B) ethanol; (C) toluene; and (D) cyclohexane. FIGS. 7A-D therefore demonstrate tuneable solubility.

Figure 8:
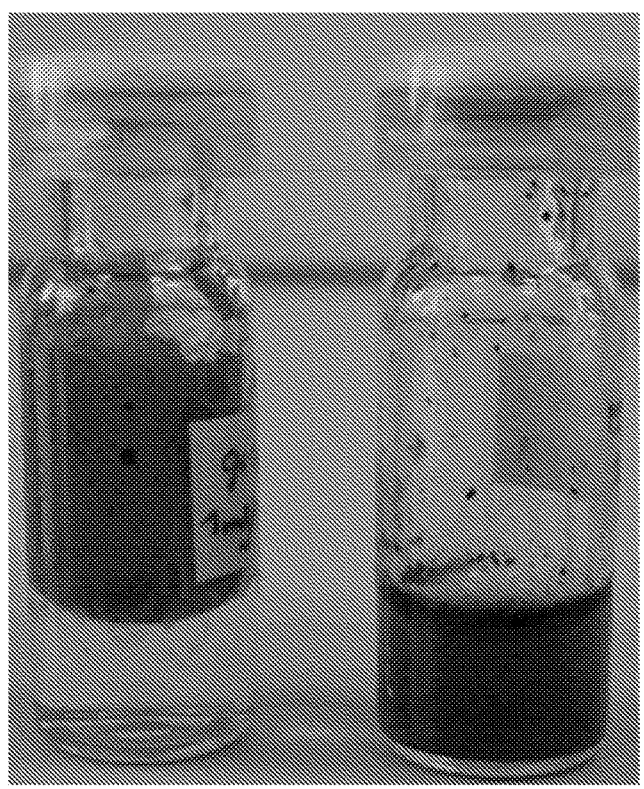
FIG. 8 shows the solubility of (left) unfunctionalised graphene and (right) glyco graphene in phosphate buffered saline.

FIG. 8 shows the solubility of (left) unfunctionalised graphene and (right) glyco graphene in phosphate buffered saline. It is clear that glyco graphene is completely clear in PBS, whereas unfunctionalised graphene sticks to the glass vial wall even after sonication.

Ellman's Reagent

Figure 9:
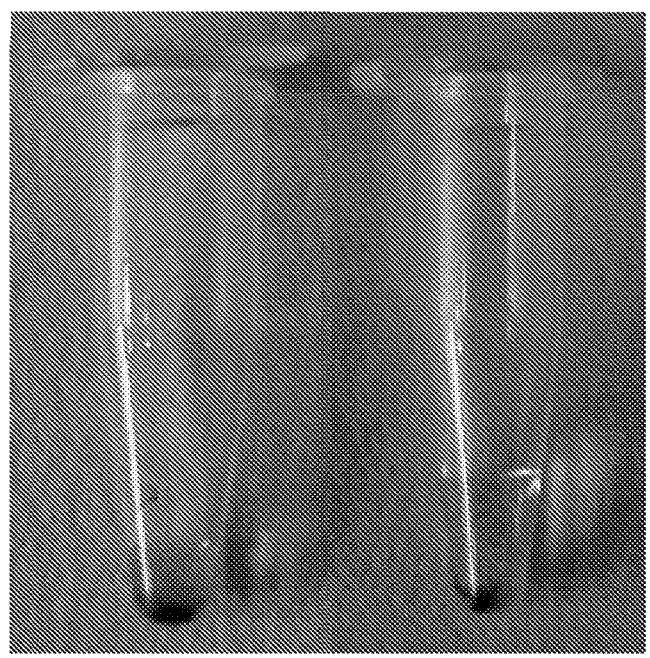
FIG. 9 shows the reaction of (left) sulpho graphene; and (right) thio graphene with Ellman's reagent.

FIG. 9 shows the reaction of (left) sulpho graphene; and (right) thio graphene with Ellman's reagent. Compounds with free thio groups react with Ellman's reagent to release a yellow dye. Upon treatment with Ellman's reagent, sulpho graphene stayed colourless, whilst thio graphene induced a colour change to yellow.

Scanning Electron Microscopy

Figure 10:
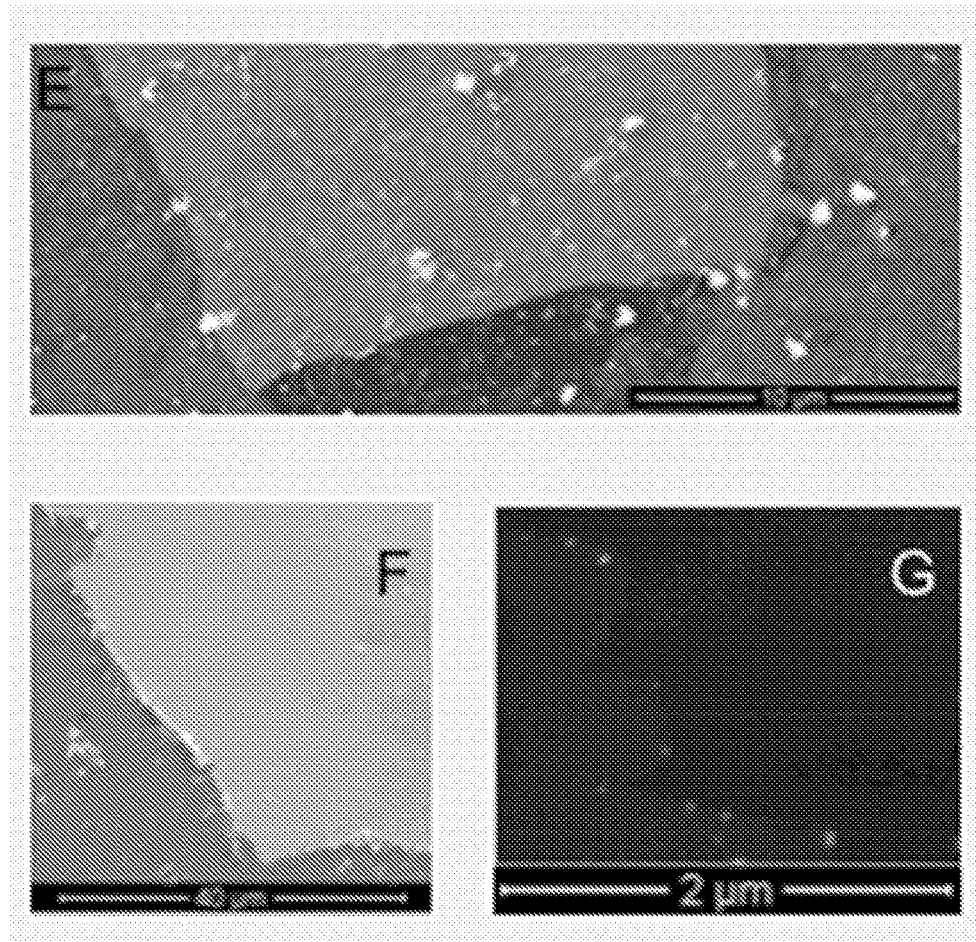
FIG. 10 shows scanning electron micrographs of (E) gold nanoparticles incubated on sulpho CVD graphene; and (F,G) gold nanoparticles incubated on thio CVD graphene.

FIG. 10 shows scanning electron micrographs of (E) gold nanoparticles incubated on sulpho CVD graphene; and (F,G) gold nanoparticles incubated on thio CVD graphene. It is clear that gold nanoparticles incubated in sulpho CVD graphene show only non-specific adsorption to the sample, whereas sulfhydryl groups predominantly localised at the edges of thio CVD graphene covalently bind the gold nanoparticles via Au—S bonds (shown as bright clusters at the edge of the thio graphene flake).

Fluorescence Microscopy

Figure 11:
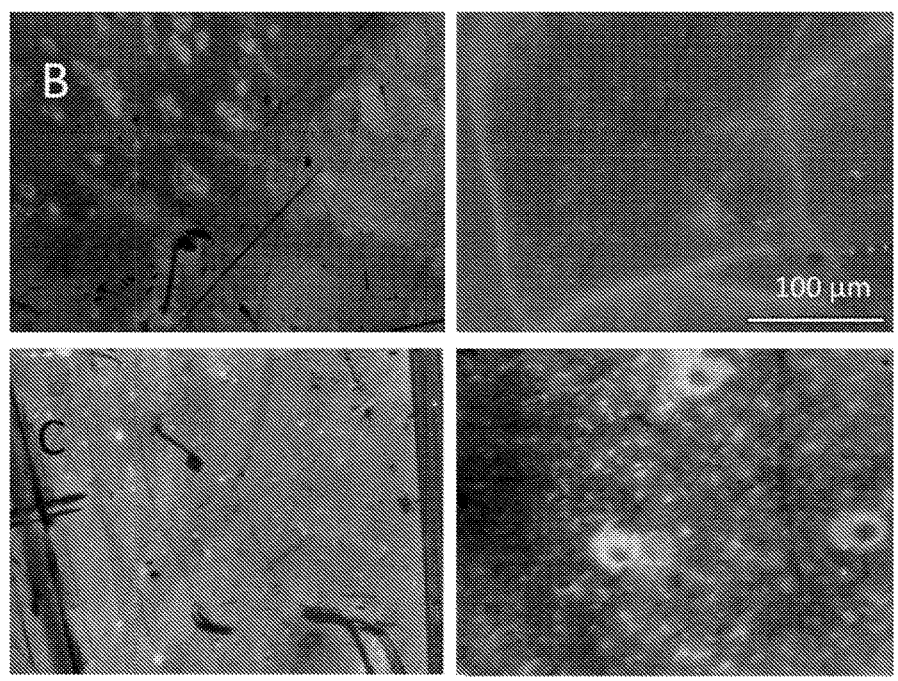
FIG. 11 shows fluorescence microscopic images of (B) (left) unfunctionalised CVD graphene and (right) glyco CVD graphene incubated with FITC-labelled (fluorescein isothiocyanate-labelled) lectin ConA; and (C) the same materials after subsequent incubation with excess methyl mannoside.

FIG. 11 shows fluorescence microscopic images of (B) (left) unfunctionalised CVD graphene and (right) glyco CVD graphene incubated with FITC-labelled lectin ConA; and (C) the same materials after subsequent incubation with excess methyl mannoside. FIG. 11A clearly shows only background fluorescence for unfunctionalised graphene, whereas fluorescent ConA can be detected around the edges of the glyco graphene flake. FIG. 11B demonstrates that after incubation of the same samples with an excess methyl mannoside as inhibitor of mannose-specific binding both samples show background fluorescence and no stronger fluorescence along the edge of the glyco graphene can be detected.

X-Ray Photoelectron Spectroscopy

Figure 12:
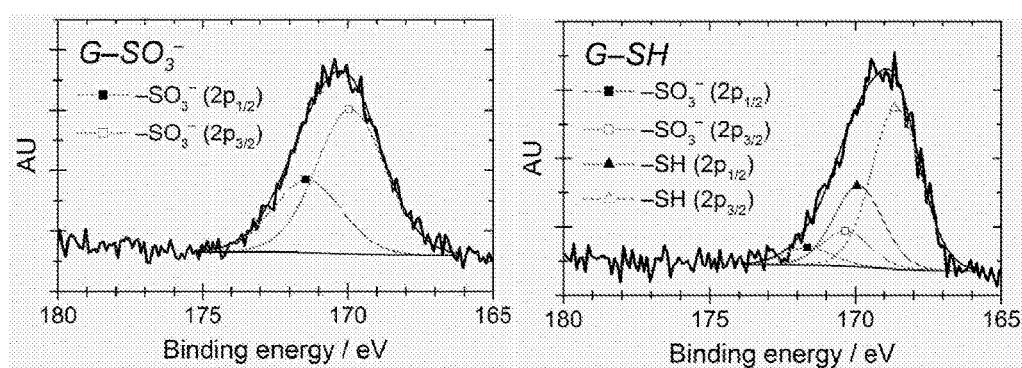
FIG. 12 shows X-ray photoelectron spectroscopy (XPS) plots from the sulphur 2p region for (left) sulpho graphene and (right) thio graphene.

FIG. 12 shows XPS plots from the sulphur 2p region for (left) sulpho graphene and (right) thio graphene. These plots demonstrate both the presence of the sulphur in the sample and identify its chemical state. The binding energy of $2p_{1/2}$ and $2p_{3/2}$ peaks in sulpho graphene matches that for aromatic sulphonates on the US National Institute of Standards and Technology (NIST) XPS database. The binding energy for these peaks in thio graphene shifts to lower energy, consistent with NIST reference data.

Lifetime Measurements of Edge-Modified Graphene with Chelated Europium(III)

The fluorescence lifetimes of europium(III) chelated by allyl DO3A were measured by exciting mixtures at 395 nm and measuring the change in emission at 614 nm with time. The decay curves were fit to one or two exponential functions. Table 2 shows the lifetime of both components of the fluorescence and how much that component contributed to the overall emission. A physical mixture of $Eu^{3+}$-allylDO3A and thiographene (i.e., one with no covalent bonds between the fluorophore and the graphene) shows a single lifetime consistent with chelated europium(III). There is no evidence of fluorescence quenching (lifetime shortening) through interactions of the complex with the graphene, for example, through adsorption on the basal plane. The sample of Eu$^{3+}$-allylDO3A covalently bound to graphene shows two lifetimes: a long one from unreacted Eu$^{3+}$-allylDO3A and a much shorter lifetime from the covalently bound complex. The much shorter lifetime shows that the complex is in good electronic contact with the graphene and that the flake is contributing to its quenching.

TABLE 2

Fluorescence lifetimes for Eu$^{3+}$-Allyl DO3A

| Sample | Lifetime 1/µs (fraction of signal) | Lifetime 2/µs (fraction of signal) |
|---|---|---|
| chelated Eu$^{3+}$ mixed with thio graphene | not observed | 358 ± 9 (100%) |
| chelated Eu$^{3+}$ bonded to thio graphene | 9.9 ± 0.6 (8.4) | 380 ± 7 (92%) |

While specific embodiments of the invention have been described herein for the purpose of reference and illustration, various modifications will be apparent to a person skilled in the art without departing from the scope of the invention as defined by the appended claims.

REFERENCES

1. Novoselov, K. S., Geim, A. K., Morozov, S. V., Jiang, D., Zhang, Y., Dubonos, S. V., Grigorieva, I. V. & Firsov, A. A. Electric Field Effect in Atomically Thin Carbon Films, *Science*, 306, 666-669 (2004). DOI: 10.1126/science.1102896
2. Berry, V. Impermeability of Graphene and its applications. *Carbon* 62, 1-10 (2013)
3. Chen, D., Tanga, L. & Li J. Graphene-based materials in electrochemistry. *Chem. Soc. Rev.* 39, 3157-3180 (2010)
4. Si, Y. & Samulski E. T. *Nano Lett.* 8, 1679-1682 (2008)
5. Hummers, W. S., Offeman, E. R. Preparation of Graphitic Oxide. *J. Am. Chem. Soc.* 80, 1339-1339 (1958). DOI: 10.1021/ja01539a017
6. Chua, C. K. & Pumera, M. Chemical reduction of graphene oxide: a synthetic chemistry viewpoint. *Chem. Soc. Rev.* 43, 291-312 (2014)
7. C. K. Chua and M. Pumera, Chem.-Asian J., 2012, 7, 1009-1012
8. Sarkar, S., Bekyarova, E., Niyogi, S. & Haddon, R. C. Diels-Alder Chemistry of Graphite and Graphene: Graphene as Diene and Dienophile. *J. Am. Chem. Soc.* 133, 3324-3327 (2011)
9. Koehler, F. M., & Stark, W. J. Organic Synthesis on Graphene. *Acc. Chem. Res.* 46, 2297-2306 (2013)
10. Le Goff, A., Reuillard, B., & Cosnier, S., A Pyrene-Substituted Tris(bipyridine)osmium(II) Complex as a Versatile Redox Probe for Characterizing and Functionalizing Carbon Nanotube- and Graphene-Based Electrodes. *Langmuir* 29, 8736-8742 (2013)
11. Kozhemyakina, N. V., Englert, J. M., Yang, G., Spiecker E., Schmidt, C. D., Hauke, F. & Hirsch, A., Non-Covalent Chemistry of Graphene: Electronic Communication with Dendronized Perylene Bisimides. *Adv. Mater.* 22, 5483-5487 (2010)
12. Jeon et al, J. Am. Chem. Soc. 2013, 135, 1386-1393.
13. Jeon et al, Sci Rep, 3: 1810, DOI: 10.1038/srep01810
14. Baek et al, J. Mater. Chem. A, 2014, 2, 8690-8695
15. Jeon et al, Sci Rep, 3:2260, DOI: 10.1038/srep02260
16. Nature Nanotechnology, 2008, 3, 563-568., J. Am. Chem. Soc., 2009, 131(10), 3611-3620
17. E. Fischer, Über die Glucoside der Alkohole. *Ber. Dtsch. Chem. Ges.* 1893, 26, 2400-2412

The invention claimed is:

1. A process for the preparation of functionalised graphene, the process comprising the steps of:
   a) preparing a sample of graphene to be functionalised,
   b) contacting the graphene with one or more reagents suitable for introducing at least one functional group selected from the group consisting of —NO$_2$, —NH$_2$, —SO$_3$H, halide, —N$_3$, —MgBr and —SH to any available edge of the sample of graphene, and
   c) isolating the functionalised graphene bearing only the at least one functional group selected from the group consisting of —NO$_2$, —NH$_2$, —SO$_3$H, halide, —N$_3$, —MgBr and —SH,
   wherein the graphene prepared in step a) is in solution, in suspension, or attached to a solid support,
   and wherein the graphene is prepared by exfoliation of graphite.

2. The process of claim 1, wherein in step b) the graphene is contacted with one or more nitrating reagents to introduce —NO$_2$ groups on the edge of the graphene, and wherein step b) further comprises a step of contacting the nitrated graphene with a reducing agent to reduce the —NO$_2$ groups to —NH$_2$ groups.

3. The process of claim 1, wherein step b) comprises contacting the graphene with one or more sulphonating agents to introduce —SO$_3$H groups onto the edge of the graphene, and wherein step b) further comprises contacting the sulphonated graphene with a reducing agent to reduce the —SO$_3$H groups to —SH groups.

4. The process of claim 1, wherein step b) is carried out over a period of 0.1-48 hours.

5. The process of claim 1, wherein the exfoliation comprises sonicating the graphite in N-methyl-2-pyrrolidone or N,N-dimethylformamide.

6. The process of claim 5, wherein the graphene is prepared by chemical vapour deposition.

7. The process of claim 6, wherein the graphene is prepared by chemical vapour deposition and then transferred to a silicon wafer coated with SiO$_2$.

8. A process for the preparation of functionalised graphene, the process comprising the steps of:
   a) preparing a sample of graphene to be functionalised,
   b) contacting the graphene with one or more reagents suitable for introducing at least one functional group selected from the group consisting of —NO$_2$, —NH$_2$, —SO$_3$H, halide, —N$_3$, —MgBr and —SH to any available edge of the sample of graphene, and
   c) isolating the functionalised graphene bearing only the at least one functional group selected from the group consisting of —NO$_2$, —NH$_2$, —SO$_3$H, halide, —N$_3$, —MgBr and —SH,
   wherein step c) comprises:
   i. separating the functionalised graphene from one or more residual reagents by filtration, following by sonicating the isolated functionalised graphene to provide a suspended solution, or
   ii. washing the functionalised graphene with at least one solvent, followed by drying the functionalised graphene.

9. The process of claim 8, wherein step c) i) further comprises lyophilising the suspended solution to a dry powder.

10. The process of claim 8, wherein step c) i) comprises separating the functionalised graphene from one or more residual reagents by filtration using a porous membrane.

11. The process of claim 8, wherein step c) ii) comprises drying the functionalized graphene in a stream of inert gas.

* * * * *